United States Patent
Carling et al.

(10) Patent No.: US 6,500,828 B1
(45) Date of Patent: Dec. 31, 2002

(54) TRIAZOLO-PYRIDAZINE DERIVATIVES AS LIGANDS FOR GABA RECEPTORS

(75) Inventors: William Robert Carling, Bishops Stortford (GB); Jose Luis Castro Pineiro, Bishops Stortford (GB); Richard Thomas Lewis, Bishops Stortford (GB); Kevin William Moore, Buntingford (GB); Leslie Joseph Street, Little Hallingbury (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/890,000

(22) PCT Filed: Jan. 19, 2000

(86) PCT No.: PCT/GB00/00183

§ 371 (c)(1),
(2), (4) Date: Jul. 23, 2001

(87) PCT Pub. No.: WO00/44752

PCT Pub. Date: Aug. 3, 2000

(30) Foreign Application Priority Data

Jan. 27, 1999 (GB) .............................................. 9901743
Jan. 27, 1999 (GB) .............................................. 9901744
May 27, 1999 (GB) .............................................. 9912429

(51) Int. Cl.$^7$ ................... A61K 31/5025; C07D 487/14
(52) U.S. Cl. ...................................... 514/248; 544/236
(58) Field of Search ........................... 544/236; 514/248

(56) References Cited

U.S. PATENT DOCUMENTS 6,255,305 B1 * 7/2001 Broughton et al. ......... 514/248

FOREIGN PATENT DOCUMENTS

WO    WO 98/04559    2/1998

OTHER PUBLICATIONS

L. J. Bristow et al., JPET, 279:492–501 (1996).
K. A. Wafford et al., Molecular Pharmacology, 50:670–678 (1996).
P. J. Baley et al., J. Psychopharmacology, 10(3):206–213 (1996).
G. R. Dawson et al., Psychopharmacology, 121:109–117 (1995).

* cited by examiner

*Primary Examiner*—Emily Bernhardt
(74) *Attorney, Agent, or Firm*—J. Eric Thies; Melvin Winokur

(57) ABSTRACT

1,2,4-triazolo[4,3-b]pyridazine derivatives, possessing a difluoro-or tri-fluoro-substituted phenyl ring at the 3-position, a triazolyl moiety at the 6-position, and a tert-butyl group at the 7-position, are selective ligands for $GABA_A$ receptors, in particular having high affinity for the $\alpha2$ and/or $\alpha3$ subunit thereof, and are useful in the treatment of anxiety and convulsions.

9 Claims, No Drawings

TRIAZOLO-PYRIDAZINE DERIVATIVES AS LIGANDS FOR GABA RECEPTORS

This application is a 371 of PCT/GB00/00183 and claims priority from Great Britain Application No. 9912429.9, filed May 27, 1999, Great Britain Application No. 9901744.4, filed Jan. 27, 1999, and Great Britain Application No. 9901743.6, filed Jan. 27, 1999.

BACKGROUND OF THE INVENTION

The present invention relates to a class of substituted triazolo-pyridazine derivatives and to their use in therapy. More particularly, this invention is concerned with substituted 1,2,4-triazolo[4,3-b]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta2/3\gamma2$, $\alpha3\beta\gamma2/3$, $\alpha2\beta\gamma1$, $\alpha5\beta3\gamma2/3$, $\alpha6\beta\gamma2$, $\alpha6\beta\delta$ and $\alpha4\beta\delta$. Subtype assemblies containing an al subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the al subunit. Accordingly, it is considered that $GABA_A$ receptor agonists which interact more favourably with the $\alpha2$ and/or $\alpha3$ subunit than with al will be effective in the treatment of anxiety with a reduced propensity to cause sedation. Also, agents which are antagonists or inverse agonists at $\alpha1$ might be employed to reverse sedation or hypnosis caused by al agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

WO 98/04559 describes a class of substituted and 7,8-ring fused 1,2,4-triazolo[4,3-b]pyridazine derivatives which are stated to be selective ligands for $GABA_A$ receptors beneficial in the treatment and/or prevention of neurological disorders including anxiety and convulsions.

SUMMARY OF THE INVENTION

The present invention provides a class of triazolo-pyridazine derivatives which possess desirable binding properties at various GABA$_A$ receptor subtypes. The compounds in accordance with the present invention have good affinity as ligands for the α2 and/or α3 subunit of the human GABA$_A$ receptor. The compounds of this invention interact more favourably with the α2 and/or α3 subunit than with the α1 subunit. Indeed, the compounds of the invention exhibit functional selectivity in terms of a selective efficacy for the α2 and/or α3 subunit relative to the α1 subunit.

The compounds of the present invention are GABA$_A$ receptor subtype ligands having a binding affinity ($K_i$) for the α2 and/or α3 subunit, as measured in the assay described hereinbelow, of less than 1 nM. Furthermore, the compounds in accordance with this invention exhibit functional selectivity in terms of a selective efficacy for the α2 and/or α3 subunit relative to the α1 subunit. Moreover, the compounds according to the present invention possess interesting pharmacokinetic properties, notably in terms of improved oral bioavailability.

DETAILED DESCRIPTION OF THE INVENTION

The present invention provides a compound of formula I, or a pharmaceutically acceptable salt thereof:

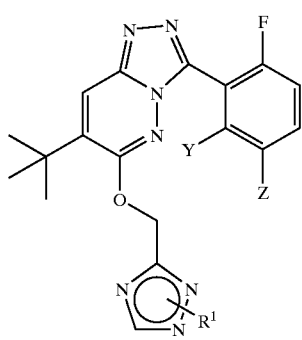

(I)

wherein

Y represents hydrogen and Z represents fluoro, or Y represents fluoro and Z represents hydrogen or fluoro; and $R^1$ represents methyl or ethyl.

The compounds in accordance with the present invention are encompassed within the generic scope of WO 98/04559. There is, however, no specific disclosure therein of compounds corresponding to those of formula I as defined above.

For use in medicine, the salts of the compounds of formula I above will be pharmaceutically acceptable salts. Other salts may, however, be useful in the preparation of the compounds of formula I or of their pharmaceutically acceptable salts. Suitable pharmaceutically acceptable salts of the compounds of formula I include acid addition salts which may, for example, be formed by mixing a solution of the compound of formula I with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

The present invention also provides a compound of formula I as depicted above, or a pharmaceutically acceptable salt thereof, wherein Y and Z both represent fluoro; and $R^1$ represents methyl or ethyl.

A particular sub-class of the compounds in accordance with the invention is represented by the compounds of formula IA, and pharmaceutically acceptable salts thereof:

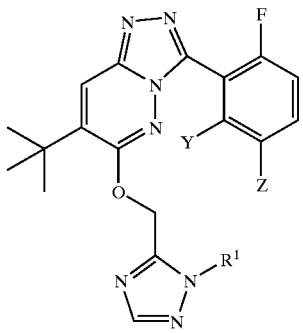

(IA)

wherein Y, Z and $R^1$ are as defined above.

Specific sub-classes of the compounds in accordance with the invention are represented by the compounds of formula IIA, IIB, and IIC, and pharmaceutically acceptable salts thereof.

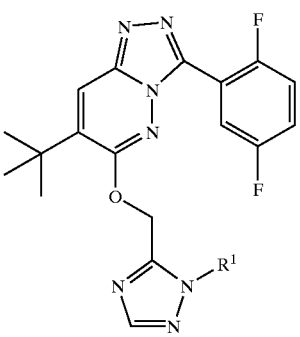

(IIA)

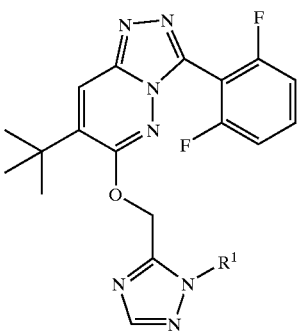

(IIB)

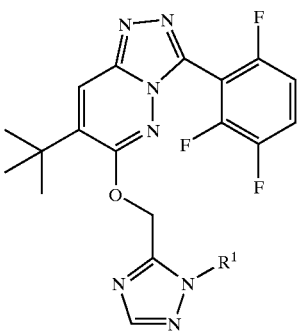

(IIC)

wherein $R^1$ is as defined above.

In one embodiment of the compounds according to the invention, the moiety $R^1$ represents methyl.

In another embodiment of the compounds according to the invention, the moiety $R^1$ represents ethyl.

Specific compounds within the scope of the present invention include:

3-(2,5-difluorophenyl)-7-(1,1-dimethylethyl)-6-(2-methyl-2H-1,2,4-triazol-3-ylmethoxy)-1,2,4-triazolo[4,3-b]pyridazine;

3-(2,5-difluorophenyl)-7-(1,1-dimethylethyl)-6-(2-ethyl-2H-1,2,4-triazol-3-ylmethoxy)-1,2,4-triazolo[4,3-b]pyridazine;

3-(2,6-difluorophenyl)-7-(1,1-dimethylethyl)-6-(2-ethyl-2H-1,2,4-triazol-3-ylmethoxy)-1,2,4-triazolo[4,3-b]pyridazine;

7-(1,1-dimethylethyl)-6-(2-ethyl-2H-1,2,4-triazol-3-ylmethoxy)-3-(2,3,6-trifluorophenyl)-1,2,4-triazolo[4,3-b]pyridazine;

7-(1,1-dimethylethyl)-6-(2-methyl-2H-1,2,4-triazol-3-ylmethoxy)-3-(2,3,6-trifluorophenyl)-1,2,4-triazolo[4,3-b]pyridazine;

7-(1,1-dimethylethyl)-6-(1-methyl-1H-1,2,4-triazol-3-ylmethoxy)-3-(2,3,6-trifluorophenyl)-1,2,4-triazolo[4,3-b]pyridazine;

and pharmaceutically acceptable salts thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is less than 1 nM.

The compounds according to the present invention elicit a selective potentiation of the GABA $EC_{20}$ response in stably transfected recombinant cell lines expressing the α3 subunit of the human $GABA_A$ receptor relative to the potentiation of the GABA $EC_{20}$ response elicited in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121,109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

Since they elicit behavioural effects, the compounds of the invention plainly are brain-penetrant; in other words, these compounds are capable of crossing the so-called "blood-brain barrier". Advantageously, the compounds of the invention are capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

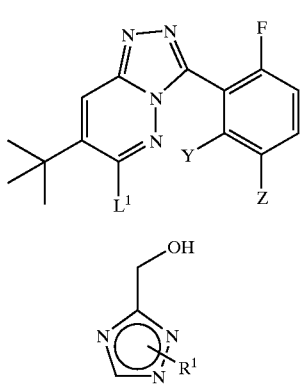

(III)

(IV)

wherein Y, Z and R¹ are as defined above, and L¹ represents a suitable leaving group.

The leaving group L¹ is typically a halogen atom, especially chloro.

The reaction between compounds III and IV is conveniently effected by stirring the reactants in a suitable solvent, in the presence of a base. Typically, the solvent is N,N-dimethylformamide, and the base is a strong base such as sodium hydride. In one preferred embodiment, the solvent is dimethylsulfoxide, and the base is caesium carbonate. In another preferred embodiment, the solvent is 1-methyl-2-pyrrolidinone, and the base is sodium hydroxide, in which case the reaction is advantageously performed at a temperature in the region of 0° C.

The intermediates of formula III above may be prepared by reacting a compound of formula V with a substantially equimolar amount of a hydrazine derivative of formula VI:

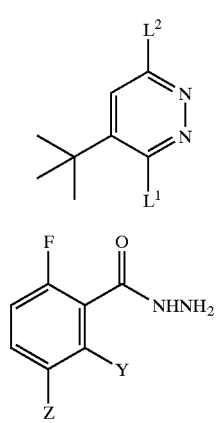

(V)

(VI)

wherein Y, Z and L¹ are as defined above, and L² represents a suitable leaving group; followed, if necessary, by separation of the resulting mixture of isomers by conventional means.

The leaving group L² is typically a halogen atom, especially chloro. In the intermediates of formula V, the leaving groups L¹ and L² may be the same or different, but are suitably the same, preferably both chloro.

The reaction between compounds V and VI is conveniently effected by heating the reactants in the presence of a proton source such as triethylamine hydrochloride, typically at reflux in an inert solvent such as xylene or 1,4-dioxane.

Alternatively, the intermediates of formula III above may be prepared by reacting a hydrazine derivative of formula VII with an aldehyde derivative of formula VIII:

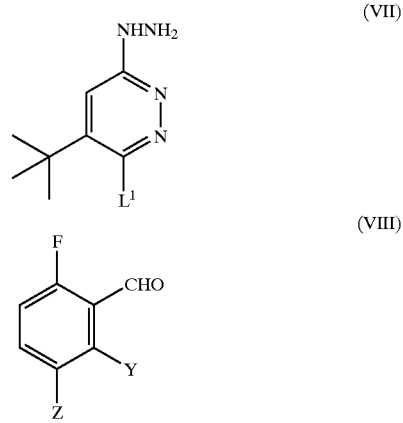

(VII)

(VIII)

wherein Y, Z and L¹ are as defined above; followed by cyclization of the intermediate Schiff's base thereby obtained.

The reaction between compounds VII and VIII is conveniently effected under acidic conditions, for example in the presence of a mineral acid such as hydrochloric acid. Cyclization of the resulting Schiff's base intermediate may then conveniently be carried out by treatment with iron(III) chloride in a suitable solvent, e.g. an alcoholic solvent such as ethanol, at an elevated temperature, typically at a temperature in the region of 80° C.

The intermediates of formula VII above may be prepared by reacting the appropriate compound of formula V as defined above with hydrazine hydrate, typically in isobutyl alcohol at an elevated temperature, e.g. a temperature in the region of 90° C., or in 1,4-dioxane or ethanol at the reflux temperature of the solvent; followed, if necessary, by separation of the resulting mixture of isomers by conventional means.

In an alternative approach, the intermediates of formula III above may be prepared by reacting the hydrazine derivative of formula VII as defined above with a compound of formula IX:

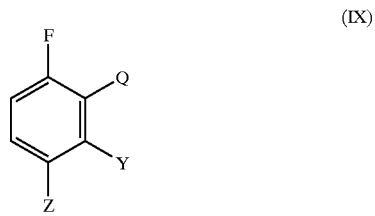

(IX)

wherein Y and Z are as defined above, and Q represents a reactive carboxylate moiety; followed, if necessary, by cyclization of the hydrazide derivative of formula X thereby obtained:

(X)

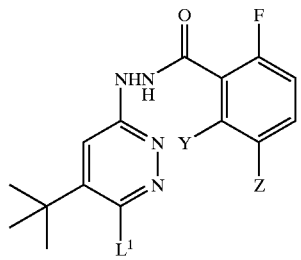

wherein Y, Z and $L^1$ are as defined above.

Suitable values for the reactive carboxylate moiety Q include esters, for example $C_{1-4}$ alkyl esters; acid anhydrides, for example mixed anhydrides with $C_{1-4}$ alkanoic acids; acid halides, for example acid chlorides; and acylimidazoles. Suitably, Q represents an acid chloride moiety.

The reaction between compounds VII and IX is conveniently effected by heating in a solvent such as 1-methyl-2-pyrrolidinone to a temperature typically in the region of 160° C.

Alternatively, the reaction between compounds VII and IX may be effected under basic conditions, e.g. in the presence of triethylamine, suitably in an inert solvent such as diethyl ether, and typically at a temperature in the region of 0° C. Cyclization of the resulting compound of formula X may then conveniently be carried out by treatment with 1,2-dibromo-1,1,2,2-tetrachloroethane and triphenylphosphine, in the presence of a base such as triethylamine, suitably in an inert solvent such as acetonitrile, and typically at a temperature in the region of 0° C.

The reaction between compound V and hydrazine hydrate or compound VI will, as indicated above, possibly give rise to a mixture of isomeric products depending upon whether the hydrazine nitrogen atom displaces the leaving group $L^1$ or $L^2$. Thus, in addition to the required product of formula III, the isomeric compound wherein the hydrazine moiety displaces the leaving group $L^1$ will possibly be obtained to some extent; and likewise for compound VII. For this reason it might be necessary to separate the resulting mixture of isomers by conventional methods such as chromatography.

In another procedure, the compounds of formula I as defined above may be prepared by a process which comprises reacting a compound of formula XI (or its 1,2,4-triazolo[4,3-b]pyridazin-6-one tautomer) with a compound of formula XII:

(XI)

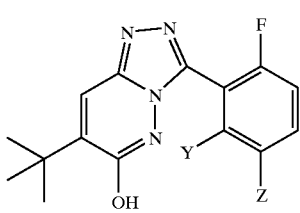

(XII)

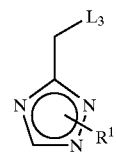

wherein Y, Z and $R^1$ are as defined above, and $L^3$ represents a suitable leaving group.

The leaving group $L^3$ is suitably a halogen atom, typically chloro or bromo.

The reaction between compounds XI and XII is conveniently effected by stirring the reactants in a suitable solvent, typically N,N-dimethylformamide, in the presence of a strong base such as sodium hydride.

The intermediate of formula XI above may conveniently be prepared by reacting a compound of formula III as defined above with an alkali metal hydroxide, e.g. sodium hydroxide. The reaction is conveniently effected in an inert solvent such as aqueous 1,4-dioxane, ideally at the reflux temperature of the solvent.

In a further procedure, the compounds of formula I as defined above may be prepared by a process which comprises reacting trimethylacetic acid with a compound of formula XIII:

(XIII)

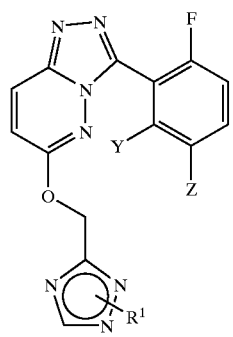

wherein Y, Z and $R^1$ are as defined above; in the presence of silver nitrate and ammonium persulphate.

The reaction is conveniently carried out in a suitable solvent, for example water or aqueous acetonitrile, optionally under acidic conditions, e.g. using trifluoroacetic acid or sulphuric acid, typically at an elevated temperature.

The intermediates of formula XIII correspond to the compounds of formula I as defined above wherein the tert-butyl substituent at the 7-position is absent, and they may therefore be prepared by methods analogous to those described above for preparing the corresponding compounds of formula I.

In a still further procedure, the compounds of formula I as defined above may be prepared by a process which comprises reacting a compound of formula XIV with a compound of formula XV:

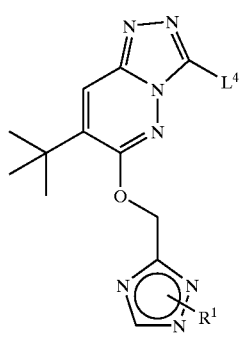

(XIV)

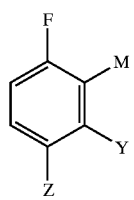

(XV)

wherein Y, Z and $R^1$ are as defined above, M represents —$B(OH)_2$ or —$Sn(Alk)_3$ in which Alk represents a $C_{1-6}$ alkyl group, typically n-butyl, and $L^4$ represents a suitable leaving group; in the presence of a transition metal catalyst.

The leaving group $L^4$ is suitably a halogen atom, e.g. bromo.

A suitable transition metal catalyst of use in the reaction between compounds XIV and XV comprises dichlorobis(triphenylphosphine)palladium(II) or tetrakis(triphenylphosphine)palladium(0).

The reaction between compounds XIV and XV is conveniently effected in an inert solvent such as N,N-dimethylformamide, typically at an elevated temperature.

The intermediates of formula XIV may be prepared by reacting a compound of formula IV as defined above with a compound of formula XVI:

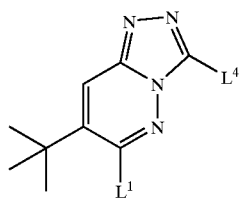

(XVI)

wherein $L^1$ and $L^4$ are as defined above; under conditions analogous to those described above for the reaction between compounds III and IV.

Where $R^1$ is methyl, the relevant intermediate of formula IV above may be prepared by the procedures described in EP-A-0421210, or by methods analogous thereto. Where $R^1$ is ethyl, the relevant intermediate of formula IV may conveniently be prepared by the method described in the accompanying Examples.

The intermediates of formula V above may be prepared by reacting trimethylacetic acid with a compound of formula XVII:

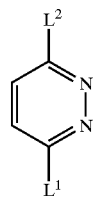

(XVII)

wherein $L^1$ and $L^2$ are as defined above; in the presence of silver nitrate and ammonium persulphate; under conditions analogous to those described above for the reaction between trimethylacetic acid and compound XIII.

Where they are not commercially available, the starting materials of formula VI, VIII, IX, XII, XV, XVI and XVII may be prepared by methods analogous to those described in the accompanying Examples, or by standard methods well known from the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk⁻ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of less than 1 nM.

EXAMPLE 1

3-(2,5-Difluorophenyl)-7-(1,1-dimethylethyl)-6-(2-methyl-2H-1,2,4-triazol-3-ylmethoxy)-1,2,4-triazolo[4,3-b]pyridazine a) 3,6-Dichloro-4-(1,1-dimethylethyl)pyridazine Concentrated sulfuric acid (53.6 ml, 1.0 mol) was added carefully to a stirred suspension of 3,6-dichloropyridazine (50.0 g, 0.34 mol) in water (1.25 l). This mixture was then heated to 70° C. (internal temperature) before the addition of trimethylacetic acid (47.5 ml, 0.41 mol). A solution of silver nitrate (11.4 g, 0.07 mol) in water (20 ml) was then added over approximately one minute. This caused the reaction mixture to become milky in appearance. A solution of ammonium persulphate (230 g, 1.0 mol) in water (0.63 l) was then added over 20–30 minutes. The internal temperature rose to approximately 85° C. During the addition the product formed as a sticky precipitate. Upon complete addition the reaction was stirred for an additional 10 minutes, then allowed to cool to room temperature. The mixture was then poured onto ice and basified with concentrated aqueous ammonia, with the addition of more ice as required to keep the temperature below 10° C. The aqueous was extracted with dichloromethane (3×300 ml). The combined extracts were dried ($MgSO_4$), filtered and evaporated to give 55.8 g of crude product as an oil. This was purified by silica gel chromatography using 0–15% ethyl acetate in hexane as eluent to give 37.31 g (53%) of the desired compound. Data for the title compound: $^1$H NMR (360 MHz, $d_6$-DMSO) δ1.50 (9H, s), 7.48 (1H, s); MS ($ES^+$) m/e 205 [MH]$^+$, 207 [MH]$^+$.

b) 3-Chloro-4-(1,1-dimethylethyl)-6-hydrazinylpyridazine

To a solution of 3,6-dichloro-4-(1,1-dimethylethyl)pyridazine (2.0 g, 9.76 mmol) in ethanol (30 ml) was added hydrazine hydrate (0.34 ml, 10.9 mmol) dropwise. The reaction mixture was heated at reflux for 18 h under an atmosphere of nitrogen. The solvent was removed under high vacuum to leave a residue to which was added 5N hydrochloric acid (50 ml). The solution obtained was washed with dichloromethane (20 ml) and the aqueous layer was poured on to a mixture of ice and aqueous ammonia. The resultant solid was collected by filtration and dried under vacuum to yield the title compound (1.2 g). Data for the title compound: $^1$H NMR (360 MHz, DMSO) δ1.39 (3H, t, J=7.3 Hz), 4.35 (2H), 7.07 (1H, s), 8.07 (1H, s); MS ($ES^+$) m/e 201, 203 [MH]$^+$.

c) 6-Chloro-3-(2,5-difluorophenyl)-7-(1,1-dimethylethyl)-1,2,4-triazolo[4,3-b]pyridazine To a slurry of 3-chloro-4-(1,1-dimethylethyl)-6-hydrazinylpyridazine (1.3 g, 6.5 mmol) in 0.1N hydrochloric acid (60 ml) was added 2,5-difluorobenzaldehyde (0.70 ml, 6.5 mmol) and the reaction mixture was stirred at room temperature for 30 minutes and then heated to 60° C. for 40 minutes. The reaction mixture was allowed to cool and the resultant solid was collected by filtration, dried and dissolved in ethanol (60 ml). To this solution was added iron(III) chloride hexahydrate (5.4 g, 32.5 mmol) in ethanol (15 ml) dropwise over 10 minutes at 80° C. The reaction mixture was stirred at 80° C. for 2 h, allowed to cool and the solvent removed by evaporation under vacuum. The residue was dissolved in dichloromethane (100 ml) and washed with water (3×100 ml), brine, dried ($MgSO_4$), filtered and concentrated under vacuum to yield the title compound (0.75 g). Data for the title compound: $^1$H NMR (250 MHz, $CDCl_3$) δ1.57 (9H, s), 7.22–7.29 (2H, m), 7.65–7.71 (1H, m), 8.19 (1H, s); MS ($ES^+$) m/e 323 [MH]$^+$.

d) 3-(2,5-Difluorophenyl)-7-(1,1-dimethylethyl)-6-(2-methyl-2H-1,2,4-triazol-3-ylmethoxy)-1,2,4-triazolo[4,3-b]pyridazine To a solution of (2-methyl-2H-1,2,4-triazol-3-yl)methanol (0.069 g, 0.4 mmol) and 6-chloro-3-(2,5-difluorophenyl)-7-(1,1-dimethylethyl)-1,2,4-triazolo[4,3-b]pyridazine (0.10 g, 0.31 mmol) in DMF (10 ml) was added sodium hydride (0.015 g of a 60% dispersion in oil, 1.2 mol eq.) and the reaction mixture was stirred at room temperature for 40 minutes. After this time the reaction mixture was diluted with water (80 ml) and the solid that precipitated was collected by filtration and washed several times with water in the sinter funnel. The solid was recrystallised from ethyl acetate/hexane to give pure title compound (0.088 g, 65%). Data for the title compound: $^1$H NMR (360 MHz, $CDCl_3$) δ1.41 (9H, s), 3.89 (3H, s), 5.54 (2H, s), 7.23–7.26 (2H, m), 7.64 (1H, m), 7.91 (1H, s), 8.00 (1H, s); MS ($ES^+$) m/e 400 [MH]$^+$. Anal. Found C, 57.36; H, 4.61; N, 24.60%. $C_{19}H_{19}F_2N_7O$ requires C, 57.14; H, 4.79; N, 24.55%.

EXAMPLE 2

3-(2,5-Difluorophenyl)-7-(1,1-dimethylethyl)-6-(2-ethyl-2H-1,2,4-triazol-3-ylmethoxy)-1,2,4-triazolo[4,3-b]pyridazine a) (2-Ethyl-2H-1,2,4-triazol-3-yl)methanol To a solution of 1,2,4-triazole (10 g, 0.145 mol) in DMF (150 ml) at room temperature was added sodium hydride (6.4 g of a 60% disp. in oil, 0.16 mol) in portions over 15 min. When the addition was complete, the reaction mixture was allowed to cool to room temperature, then cooled in an ice-bath and iodoethane (14 ml, 0.174 mol) was added dropwise over 10 mins. The reaction mixture was allowed to warm to room temperature and after stirring for 3 h the solvents were removed under high vacuum to leave a residue which was partitioned between water (300 ml) and ethyl acetate (3×300 ml). The combined organic layers were washed with saturated brine and dried ($MgSO_4$), filtered and concentrated under vacuum to leave an oily residue which was purified by distillation (120° C. @~20 mmHg) to give 1-ethyltriazole contaminated with ~15% DMF (2.4 g). The crude product (2.4 g, 0.025 mol) was dissolved in dry THF (35 ml), cooled to −40° C. and n-butyllithium (16.2 ml of a 1.6 molar solution in hexane, 0.026 mol) was added slowly over 20 mins keeping the temperature constant. DMF (2.03 ml, 0.026 mol) was then added and after 15 mins the reaction mixture was allowed to warm slowly to room temperature over 2 h. To the reaction mixture was added methanol (20 ml) followed by sodium borohydride (1 g, 0.026 mol) and the solution was allowed to stir for 14 h. The solvents were removed under vacuum and the residue was partitioned between brine (50 ml) and dichloromethane (6×50 ml). The combined organic layers were dried ($MgSO_4$), filtered and concentrated under vacuum to leave a residue which was purified by silica gel chromatography using 0–5% methanol in dichloromethane as eluent to give the title compound as an off-white solid (0.5 g, 3%). Data for the title compound: $^1$H NMR (250 MHz, CDCl$_3$) δ1.48 (3H, t, J=7.3 Hz), 4.25 (2H, q, J=7.3 Hz), 4.75 (2H, s), 5.14 (1H, br s), 7.78 (1H, s).

b) 3-(2,5-Difluorophenyl)-7-(1,1-dimethylethyl)-6-(2-ethyl-2H-1,2,4-triazol-3-ylmethoxy)-1,2,4-triazolo[4,3-b]pyridazine This compound was prepared using the procedures described in Example 1 Steps a), b), c) and d) with (2-ethyl-2H-1,2,4-triazol-3-yl)methanol used instead of (2-methyl-2H-1,2,4-triazol-3-yl)methanol in Step c). Data for the title compound: $^1$H NMR (360 MHz, CDCl$_3$) δ1.40 (9H, s), 1.47 (3H, t, J=7.3 Hz), 4.20 (2H, q, J=14.6 & 7.3 Hz), 5.54 (2H, s), 7.23–7.27 (2H, m), 7.65 (1H, m), 7.94 (1H, s), 8.00 (1H, s); MS (ES$^+$) m/e 414 [MH]$^+$. Anal. Found C, 58.17; H, 5.01; N, 23.79%. C$_{20}$H$_{21}$F$_2$N$_7$O requires C, 58.10; H, 5.12; N, 23.72%.

EXAMPLE 3

3-(2,6-Difluorophenyl)-7-(1,1-dimethylethyl)-6-(2-ethyl-2H-1,2,4-triazol-3-ylmethoxy)-1,2,4-triazolo[4,3-b]pyridazine a) 6-Chloro-3-(2,6-difluorophenyl)-7-(1,1-dimethylethyl)-1,2,4-triazolo[4,3-b]pyridazine A mixture of 3,6-dichloro-4-(1,1-dimethylethyl)pyridazine (2 g, 9.75 mmol), 2,6-difluorobenzoic acid hydrazide (2.52 g, 14.6 mmol) (WO 95/24403) and triethylamine hydrochloride (2.01 g, 14.6 mmol) in 1,4-dioxane (10 ml) was stirred and heated at reflux for 3.5 days. Upon cooling, the volatiles were removed in vacuo and the residue was triturated with dichloromethane. Any undissolved solid was removed by filtration. The residue was purified by chromatography on silica gel eluting with 0%→25% ethyl acetate in dichloromethane to give the required product (0.42 g). Data for the title compound: $^1$H NMR (250 MHz, CDCl$_3$) δ1.57 (9H, s), 7.09–7.16 (2H, m), 7.51–7.63 (1H, m), 8.19 (1H, s); MS (ES$^{30}$) m/e 323 (MH$^+$.

b) 3-(2,6-Difluorophenyl)-7-(1,1-dimethylethyl)-6-(2-ethyl-2H-1,2,4-triazol-3-ylmethoxy)-1,2,4-triazolo[4,3-b]pyridazine This compound was prepared from 6-chloro-3-(2,6-difluorophenyl)-7-(1,1-dimethylethyl)-1,2,4-triazolo[4,3-b]pyridazine and (2-ethyl-2H-1,2,4-triazol-3-yl)methanol following the procedure (sodium hydride, DMF) described in WO 98/04559. Data for the title compound: m.p. 182° C.; $^1$H NMR (400 MHz, CDCl$_3$) δ1.39–1.45 (12H, m), 4.10–4.16 (2H, m), 5.46 (2H, s), 7.09–7.15 (2H, m), 7.52–7.59 (1H, m), 7.92 (1H, s), 8.00 (1H, s); MS (ES$^{30}$) m/e 414 [MH]$^+$; Anal. Found: C, 58.19; H, 5.05; N, 23.80%. C$_{20}$H$_{21}$F$_2$N$_7$O requires: C, 58.10; H, 5.12; N, 23.72%.

EXAMPLE 4

7-(1,1-Dimethylethyl)-6-(2-ethyl-2H-1,2,4-triazol-3-ylmethoxy)-3-(2,3,6-trifluorophenyl)-1,2,4-triazolo[4,3-b]pyridazine a) 6-Chloro-7-(1,1-dimethylethyl)-3-(2,3,6-trifluorophenyl)-1,2,4-triazolo[4,3-b]pyridazine 2,3,6-Trifluorobenzoyl chloride (4.0 g) was added dropwise to a cooled (15° C.) solution of 3-chloro-4-(1,1-dimethylethyl)-6-hydrazinylpyridazine (4 g) in dry 1-methyl-2-pyrrolidinone (50 ml). After the addition the reaction mixture was heated at 160° C. for 24 h. The reaction mixture was cooled to room temperature, diluted with ethyl acetate (200 ml), and washed twice with water (200 ml). The organic phase was separated, dried (sodium sulfate), and evaporated at reduced pressure. The residue was crystallised from dichloromethane on dilution with diethyl ether to afford the title compound (5.3 g) as a colourless solid: $^1$H NMR (400 MHz, DMSO-d$_6$) δ1.52 (9H, s), 7.50 (1H, m), 7.92 (1H, m), 8.45 (1H, s); MS (ES$^{30}$) m/z 341/343 [MH]$^+$.

b) (2-Ethyl-2H-1,2,4-triazol-3-yl)methanol: alternative procedure 1,2,4-Triazole (100.0 g, 1.45 mol) in anhydrous THF (950 ml) was cooled to 0° C. and 1,8-diazabicyclo[5.4.0]undec-7-ene (DBU) (220 g, 1.45 mol) was added in one portion. The reaction mixture was stirred for 30 min until complete dissolution was observed. Whilst maintaining the ice/water cooling bath, iodoethane (317 g, 2.03 mol) was added dropwise over a 15 min period resulting in an internal temperature rise to 30° C. The reaction was stirred at room temperature for 16 h, after which the DBU hydroiodide was removed by filtration. The filtrate was cooled to −75° C. under an atmosphere of dry nitrogen. Hexyllithium (458 ml of 33% solution in hexanes) was added dropwise over 25 min keeping the internal temperature below −55° C. The reaction mixture was aged for 30 min (back to −75° C.) and then dry N,N-dimethylformamide (108 ml, 1.39 mol) was added dropwise over 10 min maintaining internal temperature below −60° C. The reaction mixture was aged at −70° C. for 90 min, then allowed to warm to 0° C. over 30 min. Ethanol (340 ml) was added over 10 min. Sodium borohydride (26.3 g, 0.695 mol) was then added portionwise maintaining the internal temperature below 6° C. After the addition the reaction mixture was allowed to warm to room temperature and stirred for 1 h. 2M H$_2$SO$_4$ (200 ml) was then added slowly with caution and the mixture stirred at room temperature for 20 h. The reaction mixture was concentrated to 675 ml and sodium sulfate (135 g) was added in one portion. The reaction mixture was warmed to 35° C. and stirred for 15 min. The solution was extracted with warm (45° C.) isobutyl alcohol (2×675 ml). The combined organic fractions were concentrated under reduced pressure to a volume of approximately 450 ml at which point the product crystallised. Heptane (1,125 l) was added and the slurry concentrated under reduced pressure to remove most of the isobutyl alcohol. Heptane was added to give a final slurry volume of 680 ml. After cooling to 0° C., filtration gave the title compound (137 g, 74% from 1,2,4-triazole). $^1$H NMR as for Example 2 Step a).

c) 7-(1,1-Dimethylethyl)-6-(2-ethyl-2H-1,2,4-triazol-3-ylmethoxy)-3-(2,3,6-trifluorophenyl)-1,2,4-triazolo[4,3-b]pyridazine To the product of Step a) (2.60 g) and the foregoing product (1.0 g) in dry dimethylsulfoxide (10 ml) was added caesium carbonate (3.05 g), and the mixture stirred at 50° C. under an atmosphere of dry nitrogen for 24 hours. On cooling to room temperature, the mixture was partitioned between ethyl acetate and water. The organic phase was separated, washed with water, evaporated at reduced pressure, and the residue chromatographed on silica gel (eluent 2.5% methanol-dichloromethane). The product was crystallised from ethyl acetate/diethyl ether/isohexane, to afford the title compound as a colourless solid. $^1$H NMR (400 MHz, DMSO-d$_6$) δ1.26 (3H, t, J=7.1 Hz), 1.38 (9H, s), 4.10 (2H, q, J=7.1 Hz), 5.53 (2H, s), 7.46 (1H, m), 7.88 (1H, m), 7.94 (1H, s), 8.18 (1H, s); MS (ES$^+$) m/z 432 [MH]$^+$.

EXAMPLE 5

7-(1,1-Dimethylethyl)-6-(2-methyl-2H-1,2,4-triazol-3-ylmethoxy)-3-(2,3,6-trifluorophenyl)-1,2,4-triazolo[4,3-b]pyridazine To the product of Example 4 Step a) (2.67 g) and (2-methyl-2H-1,2,4-triazol-3-yl)methanol (prepared as described in EP-A-421210) (0.93 g) in dry dimethylsulfoxide (10 ml) was added caesium carbonate (3.14 g), and the mixture stirred at 50° C. under an atmosphere of dry nitrogen for 24 hours. On cooling to room temperature, the mixture was partitioned between ethyl acetate and water. The organic phase was separated, washed with water, evaporated at reduced pressure, and the residue chromatographed on silica gel (eluent 2.5% methanol-dichloromethane). The product was crystallised from ethyl acetate/diethyl ether/isohexane, to afford the title compound as a colourless solid. $^1$H NMR (500 MHz, DMSO-$_6$) δ1.39 (9H, s), 3.74 (3H, s), 5.50 (2H, s), 7.46 (1H, m), 7.88 (1H, m), 7.90 (1H, s), 8.17 (1H, s); MS (ES$^+$) m/z 418 [MH]$^+$.

EXAMPLE 6

7-(1,1-Dimethylethyl)-6-(1-methyl-1H-1,2,4-triazol-3-ylmethoxy)-3-(2,3,6-trifluorophenyl)-1,2,4-triazolo[4,3-b]pyridazine To the product of Example 4 Step a) (0.559 g) and (1-methyl-1H-1,2,4-triazol-3-yl)methanol (prepared as described in EP-A-421210) (0.20 g) in dry dimethylsulfoxide (2 ml) was added caesium carbonate (0.67 g), and the mixture stirred at 60° C. under an atmosphere of dry nitrogen for 48 hours. On cooling to room temperature, the mixture was partitioned between ethyl acetate and water. The organic phase was separated, washed with water, evaporated at reduced pressure, and the residue chromatographed on silica gel (eluent 2% methanol-dichloromethane). The product was crystallised from ethyl acetate/diethyl ether, to afford the title compound as a colourless solid. $^1$H NMR (400 MHz, DMSO-d$_6$) δ1.39 (9H, s), 3.85 (3H, s), 5.30 (2H, s), 7.46 (1H, m), 7.86 (1H, m), 8.14 (1H, s) 8.46 (1H, s); MS (ES$^+$) m/z 418 [MH]$^+$.

What is claimed is:

1. A compound of formula I, or a pharmaceutically acceptable salt thereof:

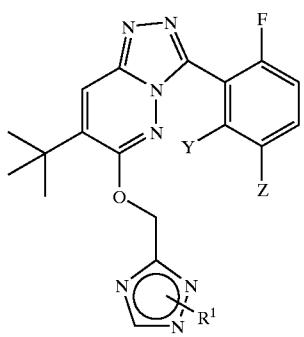

wherein

Y represents fluoro and Z represents fluoro; and

R$^1$ represents methyl or ethyl.

2. A compound as claimed in claim 1 represented by formula IA, and pharmaceutically acceptable salts thereof:

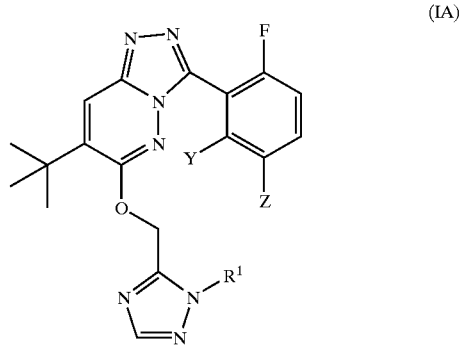

(IA)

wherein Y, Z and R$^1$ are as defined in claim 1.

3. A compound as claimed in claim 1 represented by formula IIC, and pharmaceutically acceptable salts thereof:

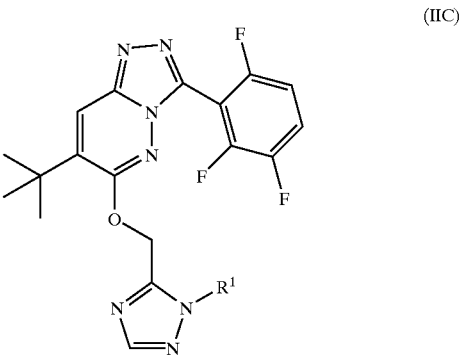

(IIC)

wherein R$^1$ is as defined in claim 1.

4. A compound as claimed in claim 1 wherein R$^1$ represents methyl.

5. A compound as claimed in claim 1 wherein R$^1$ represents ethyl.

6. A compound selected from:

7-(1,1-dimethylethyl)-6-(2-ethyl-2H-1,2,4-triazol-3-ylmethoxy)-3-(2,3,6-trifluorophenyl)-1,2,4-triazolo[4,3-b]pyridazine;

7-(1,1-dimethylethyl)-6-(2-methyl-2H-1,2,4-triazol-3-ylmethoxy)-3-(2,3,6-trifluorophenyl)-1,2,4-triazolo[4,3-b]pyridazine;

7-(1,1-dimethylethyl)-6-(1-methyl-1H-1,2,4-triazol-3-ylmethoxy)-3-(2,3,6-trifluorophenyl)-1,2,4-triazolo[4,3-b]pyridazine;

and pharmaceutically acceptable salts thereof.

7. A pharmaceutical composition comprising a compound of formula I as defined in claim 1 or a pharmaceutically acceptable salt thereof in association with a pharmaceutically acceptable carrier.

8. A process for the preparation of a compound as claimed in claim 1, which comprises:

(A) reacting a compound of formula III with a compound of formula IV:

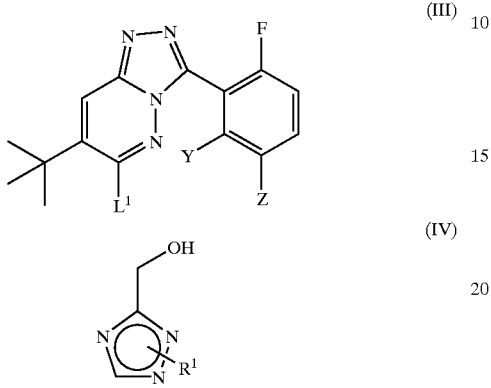

wherein Y, Z and $R^1$ are as defined in claim 1, and $L^1$ represents a suitable leaving group; or (B) reacting a compound of formula XI (or its 1,2,4-triazolo[4,3-b]pyridazin-6-one tautomer) with a compound of formula XII:

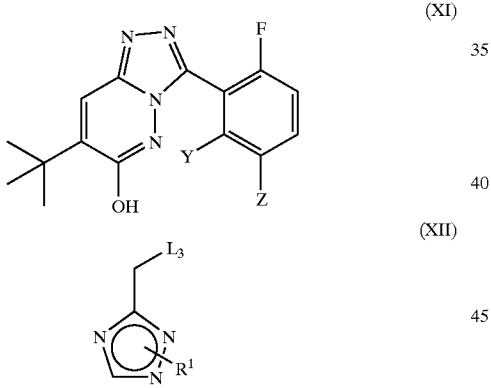

wherein Y, Z and $R^1$ are as defined in claim 1, and $L^3$ represents a suitable leaving group; or (C) reacting trimethylacetic acid with a compound of formula XIII:

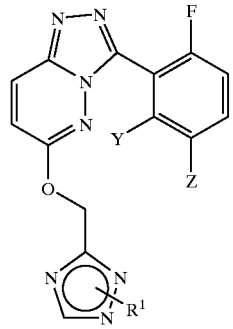

wherein Y, Z and $R^1$ are as defined in claim 1; in the presence of silver nitrate and ammonium persulphate; or (D) reacting a compound of formula XIV with a compound of formula XV:

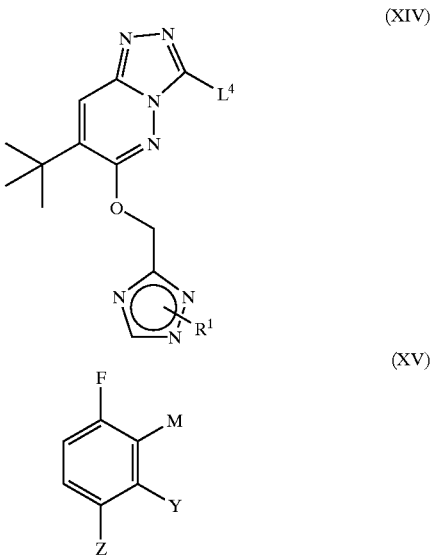

wherein Y, Z and $R^1$ are as defined in claim 1, M represents —B(OH)$_2$ or —Sn(Alk)$_3$ in which Alk represents a $C_{1-6}$ alkyl group, and $L^4$ represents a suitable leaving group; in the presence of a transition metal catalyst.

9. A method for the treatment and/or prevention of anxiety which comprises administering to a patient in need of such treatment an effective amount of a compound of formula I as defined in claim 1 or a pharmaceutically acceptable salt thereof.

* * * * *